US007823843B2

(12) United States Patent
Oberlaender et al.

(10) Patent No.: US 7,823,843 B2
(45) Date of Patent: Nov. 2, 2010

(54) SURGICAL ARMREST

(75) Inventors: Martin Oberlaender, Engen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 924 days.

(21) Appl. No.: 11/626,243

(22) Filed: Jan. 23, 2007

(65) Prior Publication Data

US 2007/0170767 A1 Jul. 26, 2007

(30) Foreign Application Priority Data

Jan. 25, 2006 (DE) ...................... 10 2006 004 126

(51) Int. Cl.
*A61G 13/00* (2006.01)

(52) U.S. Cl. ................ 248/118; 248/278.1; 248/276.1; 248/284.1; 5/621; 5/623

(58) Field of Classification Search ............. 248/118.1, 248/118.3, 118, 276.1, 278.1, 284.1, 281.11; 5/621, 623

See application file for complete search history.

(56) References Cited

U.S. PATENT DOCUMENTS

| | | | | |
|---|---|---|---|---|
| 3,124,328 | A | 3/1964 | Kortsch | 248/118 |
| 4,858,903 | A * | 8/1989 | Tari et al. | 5/623 |
| 5,074,501 | A | 12/1991 | Hölttä | 248/118 |
| 5,571,274 | A * | 11/1996 | Holstensson | 297/411.38 |
| 5,791,263 | A | 8/1998 | Watt et al. | 108/138 |

(Continued)

FOREIGN PATENT DOCUMENTS

DE 100 51 892 4/2002

(Continued)

OTHER PUBLICATIONS

European Search Report, May 8, 2007, 5 pages.

*Primary Examiner*—J. Allen Shriver, II
*Assistant Examiner*—Steven M Marsh
(74) *Attorney, Agent, or Firm*—St. Onge Steward Johnston & Reens LLC

(57) ABSTRACT

The invention relates to a surgical armrest, comprising an arm support and a carrying structure for the arm support. The carrying structure has a base and at least one pivot arm which at one end is articulated on the base so as to pivot about an at least approximately horizontal pivot axis and at the other end is connected to the arm support, such that a pivoting of the at least one pivot arm about the pivot axis causes a height adjustment of the arm support. The at least one pivot arm is assigned a control mechanism which alternately permits a fixing and pivoting of the at least one pivot arm in the downward direction and in the upward direction. The control mechanism has at least one bar which is movable, at least in its longitudinal direction, upon pivoting of the at least one pivot arm. The bar interacts with a freewheel coupling comprising a first coupling element and a second coupling element, wherein the first coupling element is driven by the bar and is freely movable relative to the second coupling element upon an upward movement of the at least one pivot arm, and, upon a downward movement of the at least one pivot arm, drives the second coupling element along with it, the second coupling element being braked by means of at least one brake element.

20 Claims, 8 Drawing Sheets

10 12 14 16 18 20 22 24 26 28 30 32 34 36 38 40 46 48 50 52 54 64 70 78 114 130 160 162

U.S. PATENT DOCUMENTS

| | | | | |
|---|---|---|---|---|
| 5,825,536 | A * | 10/1998 | Yasunaga et al. | 359/384 |
| 5,918,330 | A | 7/1999 | Navarro et al. | 5/624 |
| 6,030,130 | A * | 2/2000 | Paddock et al. | 396/421 |
| 6,102,344 | A | 8/2000 | Kasvin et al. | 248/118 |
| 6,523,796 | B2 | 2/2003 | Abramowsky et al. | 248/284 |
| 6,704,959 | B2 * | 3/2004 | Schuerch | 5/648 |
| 7,461,423 | B2 * | 12/2008 | Rutherford et al. | 5/646 |
| 7,487,563 | B2 * | 2/2009 | Rutherford et al. | 5/623 |
| 7,556,626 | B2 * | 7/2009 | Ueda et al. | 606/1 |
| 2004/0138524 | A1 | 7/2004 | Ueda et al. | 600/102 |
| 2005/0051688 | A1 | 3/2005 | Dittmer | 248/276.1 |
| 2005/0224670 | A1 | 10/2005 | Metelski | 248/280 |

FOREIGN PATENT DOCUMENTS

| | | |
|---|---|---|
| DE | 10 2004 017 970 | 10/2005 |
| EP | 1 486 178 | 12/2004 |
| EP | 1 669 038 | 6/2006 |
| WO | WO 02/28338 | 4/2002 |

* cited by examiner 12
160
50
53
52
48
58
60
62
56
54
34
36
112
102
74
72
114
64
70
100
10
42
44
80
130
14
16

20
18

62
80
82
120
126
128
56
68
122
124
64
66
56a
67
69
a)
86
b)

a)
10
12
160
146
46
48
148
144
150
152
142
132
138
A
56
140
164
134
136
154
54
34
130
80
36
32
64

62
138
134
136
A
132
124
56
69
a)
b)

SURGICAL ARMREST

CROSS-REFERENCE TO RELATED APPLICATION

The present application claims priority of German Patent Application No. 10 2006 004 126.7, filed on Jan. 25, 2006.

BACKGROUND OF THE INVENTION

The invention generally relates to surgical armrests.

A surgical armrest is used to support the arm of a surgeon or of a surgical assistant during an operation, in order to increase the precision of the surgeon's hand movements and to reduce fatigue. In view of the fact that a surgical intervention can last several hours and that the surgical personnel perform such an operation standing up, an armrest can contribute to ensuring that the precision of the manoeuvres performed by the operating surgeon does not decrease over time.

An armrest known from document U.S. Pat. No. 5,074,501 comprises an arm support which is secured on a carrying structure for the arm support. The arm support comprises a base and two pivot arms which together form a parallelogram. The two pivot arms are secured on the base in each case about a horizontally extending pivot axis, the two pivot axes of the two pivot arms being spaced apart from one another in the vertical direction.

The arm support is connected to the two pivot arms at their ends remote from the base. The height of the arm support is changed by the pivot arms being pivoted up or down.

The two pivot arms of the known armrest are assigned a control mechanism which makes it possible to pivot the pivot arms up or down and thus change the height of the arm support and to fix the pivot arms in a defined pivoting position and thus fix the arm support at a defined height. The control mechanism comprises a bar which moves at least in its longitudinal direction during pivoting of the two pivot arms.

On the upper and lower pivot arm, the bar is assigned securing clamps with which the movement of the bar can be blocked by tightening of the clamps, as a result of which the pivoting of the two pivot arms is blocked and the arm support can thus be secured at a defined height.

Such a control mechanism for lifting and lowering and for securing the arm support has the disadvantage that the securing clamps cannot be actuated by the hand of that arm resting in the arm support. For surgical applications in which the height of the arm support has to be adjusted frequently during an operation, this known armrest is only suitable to a limited degree because it is awkward to handles. In addition, it does not permit a controlled lowering of the arm support. Instead, there is a danger of the arm support dropping in an uncontrolled manner after the securing clamps have been released.

By contrast, the document EP-A-1 486 178 discloses a surgical armrest which, compared to the known armrest described above, has the advantage that the lifting, lowering and fixing of the armrest can be carried out using the arm that is received in the arm support. The control mechanism of this known surgical armrest comprises a force switch which, by means of different forces applied by the arm received in the arm support, switches an electric motor on and off, the electric motor driving a bar which allows the pivot arm to be pivoted up or down as a result of the bar being driven in or out.

The disadvantage of an electromechanical control mechanism of this kind is that a power supply is needed via a power cable. However, power cables constitute an obstacle in an operating theatre. In addition, in the event of a defect of the electric motor, for example due to overloading of the electric motor, the control mechanism does not function. If such a defect occurs during an operation, the operation has to be continued without an armrest.

In addition to drive mechanisms comprising electric motors, it has also been proposed, for example in document U.S. Pat. No. 6,102,344, to use hydraulic or pneumatic control mechanisms for adjusting the height of the arm support for surgical armrests. Like control mechanisms with electric motors, hydraulic or pneumatic control mechanisms have the disadvantage that they are not suitable for sterilization in an autoclave. Surgical instruments and appliances have to satisfy particularly stringent demands concerning their cleaning and sterilization in particular. A safe method of sterilization is the sterilization of instruments and appliances in an autoclave in which temperatures of over 120° C. and high steam pressures prevail. Electromotive, hydraulic or pneumatic parts cannot withstand these conditions.

A surgical armrest whose control mechanism operates mechanically is therefore desirable.

However, the armrest known from the document mentioned at the outset, and having a mechanically operating control mechanism, is, as has already been described, disadvantageous in terms of the lifting, lowering and fixing functions of the arm support.

SUMMARY OF THE INVENTION

The object of the invention is therefore to provide a surgical armrest having a control mechanism that is improved in terms of the aforementioned functions.

According to the invention, a surgical armrest is provided comprising an arm support and a carrying structure for carrying the arm support. The carrying structure has a base and at least one pivot arm having a first end articulated on the base so as to pivot about an at least approximately horizontal pivot axis, and a second end connected to the arm support, such that a pivoting of the at least one pivot arm about the pivot axis causes a height adjustment of the arm support. A control mechanism is provided for controlling the at least one pivot arm for alternately permitting a fixing and a pivoting of the at least one pivot arm in downward direction and in upward direction. The control mechanism has at least one bar which is movable, at least in a longitudinal direction of the bar, upon pivoting of the at least one pivot arm. The control mechanism further has a freewheel coupling having a first coupling element and a second coupling element, the first coupling element being driven by the bar and being freely movable relative to the second coupling element upon an upward movement of the at least one pivot arm, and, upon a downward movement of the at least one pivot arm, driving the second coupling element, and the second coupling element being braked by means of at least one brake element.

Accordingly, the control mechanism of the surgical armrest according to the invention is provided with a freewheel coupling that interacts with the bar in such a way that it ensures a different speed of the at least one pivot arm in the downward direction and in the upward direction. For this purpose, the freewheel coupling comprises a first coupling element which is driven by the bar during each downward and upward movement of the at least one pivot arm. During an upward movement of the at least one pivot arm, the first coupling element is freely movable relative to the second coupling element, such that the pivot arm and, consequently, the arm support can move smoothly. By contrast, during a downward movement of the at least one pivot arm for lowering the arm support, the first coupling element drives the second coupling element, and, because the latter is braked by means of a brake element, the downward movement of the at least one pivot arm is slower compared to the upward movement. This prevents the arm support from dropping in an uncontrolled manner, since the downward movement is attenuated by the brake element.

Such a freewheel coupling according to the invention can advantageously be composed of parts that withstand treatment in an autoclave, while permitting improved operating safety and manoeuvring compared to the known armrest with mechanical control mechanism.

In a preferred embodiment, the first coupling element and the second coupling element are in connection with one another via a form-fit engagement during the downward movement of the at least one pivot arm, whereas, during an upward movement of the at least one pivot arm, the form-fit engagement is cancelled by the second coupling element being spaced away from the first coupling element.

The advantage of this measure is that the different running characteristics of the pivoting of the at least one pivot arm in the upward and downward direction is effected simply by a spacing of the second coupling element from the first coupling element, by means of which the form-fit engagement between the first coupling element and second coupling element is cancelled. The form-fit engagement between the first coupling element and second coupling element during the downward movement of the at least one pivot arm ensures that no slip occurs between the first coupling element and second coupling element during this movement and thus ensures the braking action of the second coupling element for a controlled downward movement of the at least one pivot arm.

In another preferred embodiment, the first coupling element and the second coupling element are rotatable about a common rotation axis and, on their end faces directed toward one another, have a complementary oblique toothing which, in one direction of rotation of the first coupling element, causes a pushing-away of the second coupling element and, in the opposite direction of the first coupling element, causes a rotational movement of the second coupling element.

In this embodiment, the first coupling element and the second coupling element are accordingly arranged one after the other in respect of the common rotation axis, which reduces the overall space of the freewheel coupling. The complementary oblique toothing on the end faces constitutes a structurally advantageous and simple measure for creating the form-fit engagement with the second coupling element in one direction of rotation of the coupling element, whereas, in the reverse direction of rotation of the first coupling element, its oblique toothing automatically pushes away the second coupling element without the need for manual intervention, in order to ensure the free-running of the first coupling element relative to the second coupling element.

It is also preferable if the second coupling element is axially movable in the direction of the rotation axis and is pretensioned in the direction toward the first coupling element.

This measure has the advantage that after each upward movement of the at least one pivot arm, the second coupling element automatically comes into form-fit engagement again with the first coupling element, as a result of which the brake is activated again on completion of each lifting of the arm support.

In another preferred embodiment, the common rotation axis extends at least approximately perpendicular to the axial direction of movement of the bar.

The advantage of this measure lies in the space-saving construction, because the freewheel coupling in this arrangement is arranged transverse to the at least one pivot arm.

In another preferred embodiment, the bar drives the first coupling element via a gear arrangement.

The advantage of this measure is that, with a suitable configuration, a gear arrangement can provide a force transmission necessary and adapted for the driving of the freewheel coupling via the bar.

It is also preferable if the gear arrangement has at least one toothed wheel that meshes with a toothing of the bar.

The configuration of the gear arrangement with at least one toothed wheel is advantageous in terms of the ability to autoclave the control mechanism and thus the whole armrest.

It is also preferable if the gear arrangement comprises at least two toothed wheels that mesh with one another and preferably have a different diameter.

The use of at least two meshing toothed wheels, of which one meshes with the toothed bar and the other is connected to the first coupling element, has the advantage that a suitable speed of rotation transmission ratio can be selected by virtue of the different diameters of the two toothed wheels. For example, one toothed wheel with a greater diameter can mesh with the toothing of the bar, and the second toothed wheel, which for example sits on the shaft of the first coupling element, has by contrast a smaller diameter.

In another preferred embodiment, the braking action brought about by the brake element is adjustable.

This measure has the advantage that the braking action can be adapted to the particular requirements of the person using the armrest. In particular, in the event that the downward movement of the arm support is effected or assisted by the force of a spring, the braking action can be adapted to the spring force in order to set a desired speed of lowering of the arm support.

In another preferred embodiment, the brake element is made from an elastic material, and a clamping device is operatively connected to the brake element in order to vary the contact pressure of the brake element on the second coupling element.

This measure constitutes a structurally advantageous and simple possibility of adapting the braking action of the brake element to the second coupling element. For example, the clamping device can preferably have a clamping jaw and an adjustment member for the clamping jaw. The elastic material used for the brake element is preferably an autoclavable material, for example silicone.

In another preferred embodiment, the bar is assigned at least one spring which is tensioned during an upward movement of the at least one pivot arm and is relaxed during a downward movement.

The advantage of this measure is that the bar is pretensioned in the downward direction of the pivoting movement of the at least one pivot arm. The force of the spring is therefore counteracted in the upwardly directed pivoting movement of the at least one pivot arm and, thus, for the lifting of the arm support. However, the pretensioning of the bar should not be so great that the upward movement is slow. The pretensioning of the bar by means of a spring in the downward direction has the advantage that, after a catch for the bar is released, the arm support lowers automatically, but in a manner controlled by the braking action of the freewheel coupling.

For this purpose, it is also preferable if the at least one spring is configured such that the at least one pivot arm is pivoted in the downward direction by the force of the spring counter to the braking action generated by the brake element.

The pretensioning of the spring is preferably adjustable.

In a preferred embodiment, provision is also made that the carrying structure comprises at least one second pivot arm which extends at least approximately parallel to the first pivot arm and at one end is articulated on the base about a pivot axis spaced vertically apart from the pivot axis of the first pivot arm and at the other end is connected to the arm support, and that the bar is partially received in a cylinder so as to be movable relative to the latter, the cylinder being secured on the second pivot arm.

In this embodiment, the carrying structure of the surgical armrest according to similarly to the known armrest mentioned at the outset. Such a parallelogram structure of the pivot arms increases the overall stability of the armrest, particularly when the control mechanism, which includes the bar and cylinder, is disposed directly between the two pivot arms. In the context of the invention, however, it is also conceivable to use just one pivot arm, and to secure the bar on the base via the cylinder.

In another preferred embodiment, the bar is provided with a releasable catch which blocks the bar so that it is axially immovable and then frees it after release.

This measure advantageously increases the operating safety of the surgical armrest, since the catch ensures that undesired lowering of the arm support is avoided, by means of the catch blocking the axial mobility of the bar and thus the pivotability of the at least one pivot arm. In this way, the person operating the armrest can support himself safely on the arm support without any risk of the arm support dropping. In this embodiment, the arm support can be lowered only after the catch has been released.

It is also preferable if the catch is formed by a bolt which has a passage for the bar, the bolt being able to be moved about a tilt axis into a first tilt position, in which the bar extends obliquely through the passage and is thus clamped on the passage, and into a second tilt position in which the bar extends substantially perpendicularly through the passage and is thus axially movable.

The advantage of this embodiment of the releasable catch is that the bar can be blocked steplessly relative to the adopted height of the arm support. In this way, the arm support can also be arrested at any intermediate height between a lowermost position and a highest position.

It is also preferable here if the arm support is movable relative to the at least one support arm, and if the catch is connected to the arm support in such a way that, by slight lifting of the arm support relative to the at least one pivot arm, the catch is transferred from its blocked position into the release position, and, by slight lowering of the arm support relative to the at least one pivot arm, is transferred into the blocked position.

The advantage of this measure is that the catch can be released by simple manoeuvring, namely by the arm support being raised slightly. The catch is activated simply by slight lowering of the arm support relative to the at least one pivot arm, which is already done largely automatically by the force of gravity of the arm support. Preferably, the catch can additionally be pretensioned into the blocked position.

In another preferred embodiment, the arm support is designed in such a way that it allows the arm support to be lifted by the same arm that is resting on the arm support.

The advantage of this measure is that the catch can also advantageously be released using the arm that is resting in the arm support. In this way, complete use of all the degrees of freedom of the arm support is possible using the arm that is resting on the arm support, without the user needing the hand of this arm or of the other arm to actuate the surgical armrest. It is therefore possible to control all movements of the arm support using the arm received in the arm support.

In a structurally simple embodiment of the arm support, the latter is designed as a substantially C-shaped shell, such that even the top face of the arm received in the arm support is at least partially enclosed by the arm support. The C-shaped design also has the advantage that the arm can be inserted from the side into the arm support.

Further advantages and features will become apparent from the following description and from the attached drawing.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

An illustrative embodiment of the invention is shown in the drawing and is described in more detail below with reference to said drawing, in which.

DETAILED DESCRIPTION OF A PREFERRED EMBODIMENT

Figure 1:
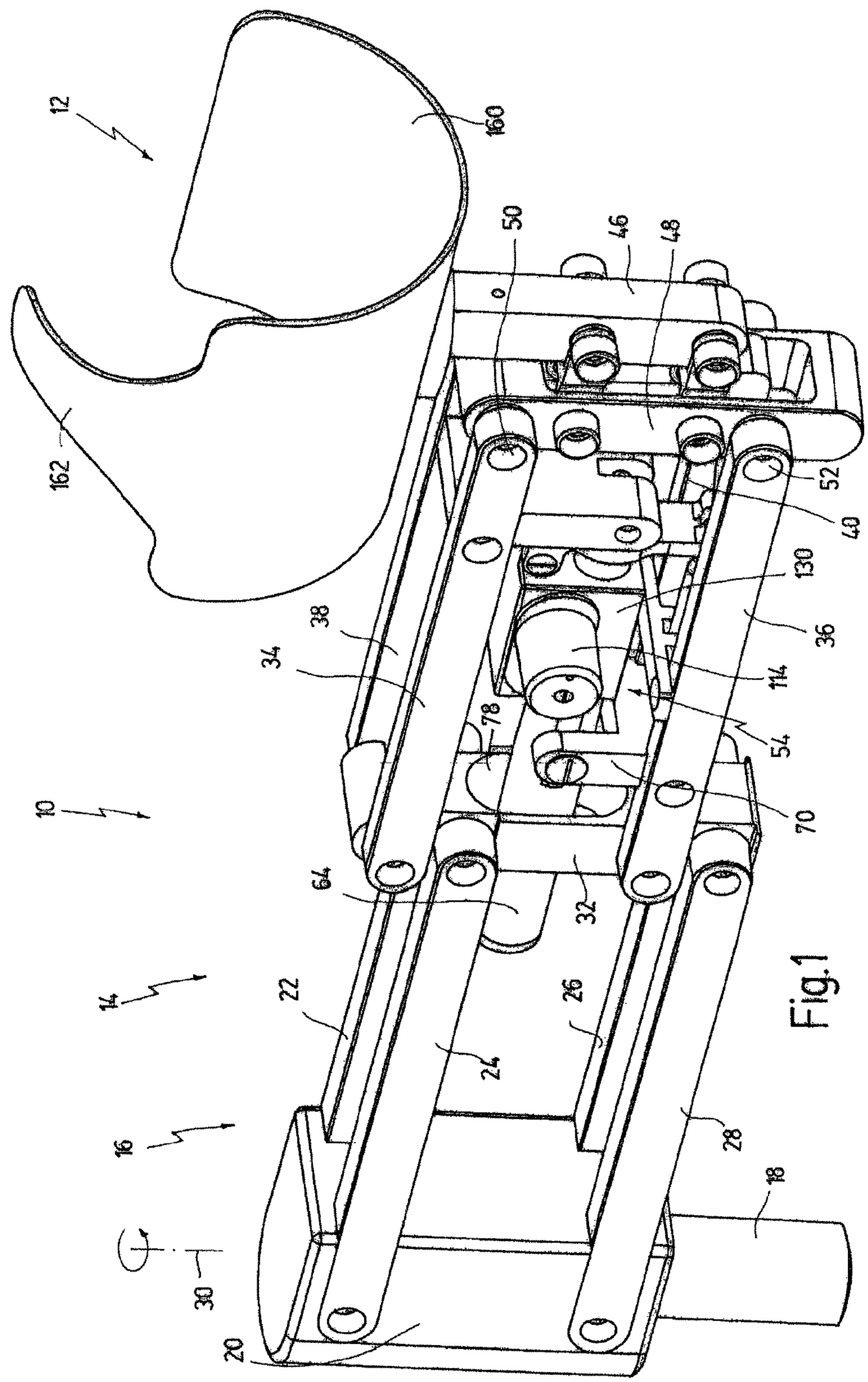
FIG. 1 shows a perspective overall view of a surgical armrest.
Figure 2:
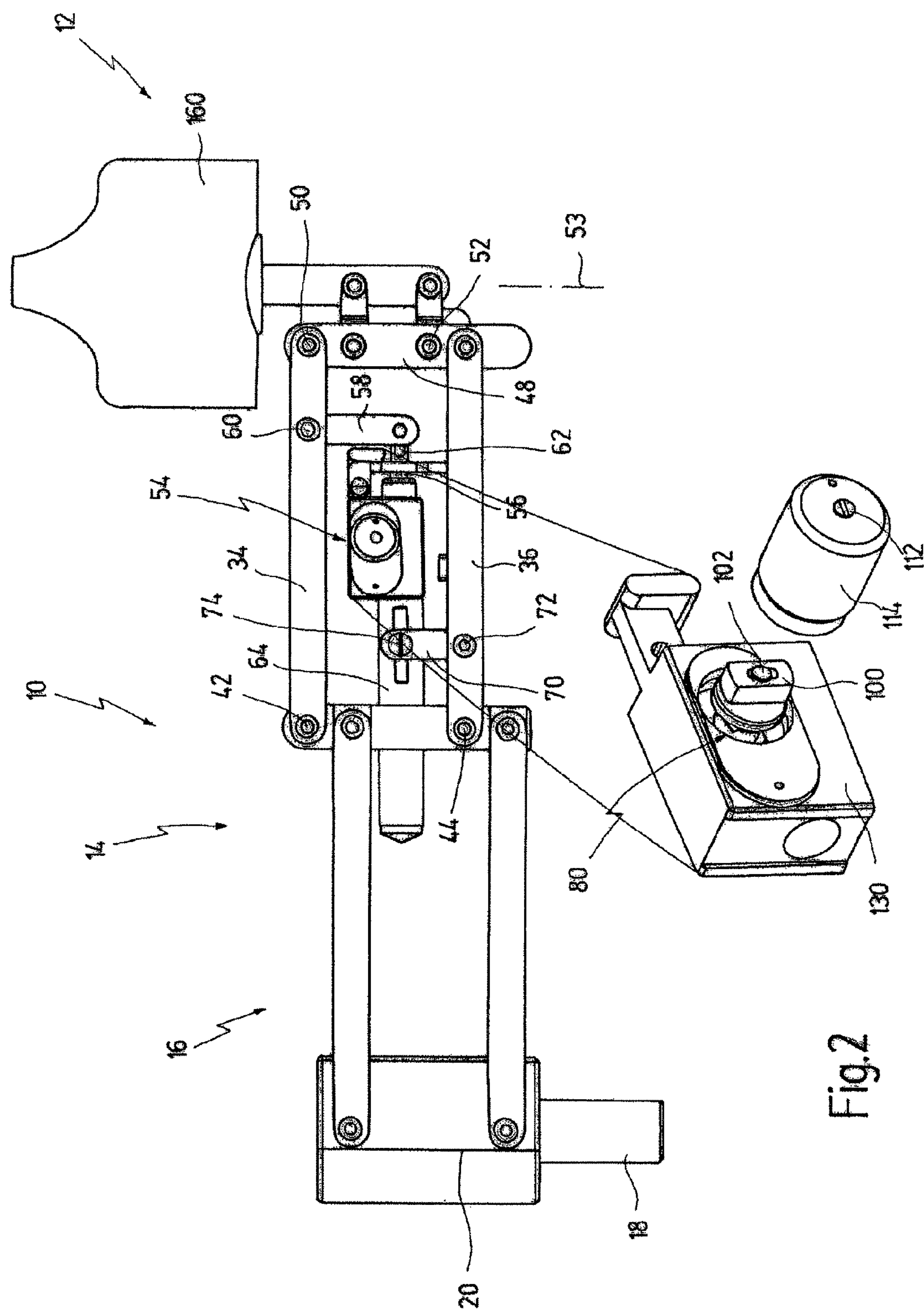
FIG. 2 shows a side view of the armrest in FIG. 1, on a reduced scale compared to FIG. 1 and depicting an enlarged detail of the armrest.

In FIGS. 1 and 2, a surgical armrest designated by the general reference number 10 is illustrated. The armrest 10 is used, during an operation, to keep the arm of a surgeon or of a surgical assistant in a selected position, and also to change this position.

The armrest 10 comprises generally an arm support 12 and a carrying structure 14 for the arm support 12.

The carrying structure 14 has a base 16 which, in the illustrative embodiment shown, has a stem 18 which is used for mounting the armrest 10 on a stand (not shown) or on an operating table (not shown). At the top of the stem 18, the latter is connected to a carrying block 20 which in turn carries at least one carrying arm or, in the illustrative embodiment shown, four carrying arms 22, 24, 26 and 28. In the illustrative embodiment shown, the carrying arms 22 to 28 are immovable relative to the carrying block 20, but they could also be mounted on the carrying block 20 so as to pivot about substantially horizontal pivot axes, so as to permit a rough preliminary setting of the height of the arm support 12.

The base 16 can in particular be rotatable about a substantially vertical axis 30, such that the arm support 12 can be pivoted in a substantially horizontal plane according to the set height.

At the ends of the carrying arms 22 to 28 remote from the carrying block 20, the base comprises a strut 32 which extends substantially vertically and on which the four carrying arms 22 to 28 are secured.

The carrying structure 14 additionally comprises at least one pivot arm or, in the illustrative embodiment shown, four pivot arms 34, 36, 38, 40, which together form a parallelogram structure.

With their ends directed toward the carrying arms 22 to 28, the pivot arms 34 to 40 are articulated so as to pivot in each case about an at least approximately horizontal pivot axis, specifically on the strut 32 of the base 16. The pivot arms 34 and 38 extend in this case parallel to one another and are articulated on the base 16 so as to pivot about a common pivot axis 42, and the pivot arms 36 and 40, which also extend parallel to one another, are pivotable about a pivot axis 44 that is vertically spaced apart from the pivot axis 42.

At their end remote from the pivot axes 42 and 44, respectively, the pivot arms 34, 38 and 36, 40 are connected to the arm support 12. In the illustrative embodiment shown, the arm support 12 is secured, by means of a substantially vertically disposed bearing element 46, on a likewise substantially vertically disposed strut 48, to which the ends of the pivot arms 34 to 40 remote from the pivot axes 42 and 44 are also connected in an articulated manner at axes 50 and 52.

The arm support 12 can be rotated about an axis 53, preferably through 360 degrees.

The arm support 12 is adjusted upward or downward by a pivoting of the pivot arms 34 to 40 about the pivot axes 42 and 44 in the upward or downward direction. To ensure a lifting of the arm support 12, a controlled lowering of the arm support 12 and a fixing of the arm support 12 in a selected height position, a control mechanism 54 is provided, which will be described below.

Figure 5:
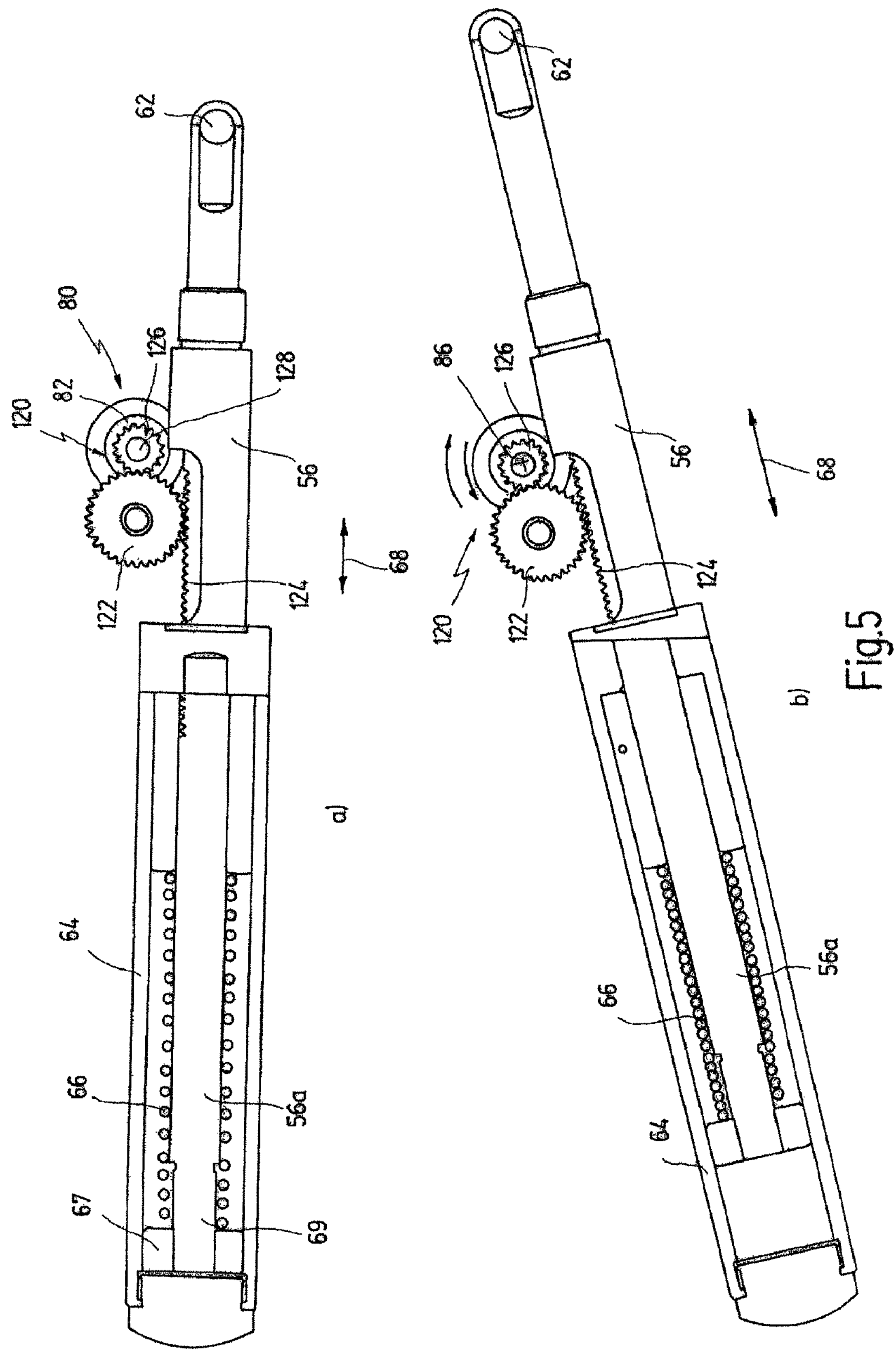
FIGS. 5*a*) and *b*) show further details of the surgical armrest in FIGS. 1 and 2 in two different operating states.

Referring first to FIGS. 2, 5*a*), *b*), 6*b*), 8*a*) and *b*), the control mechanism 54 comprises a bar 56 which is connected to the pivot arms 34 and 38. To obtain a favourable angle position of the bar 56 relative to the pivot arms 34, 38, a spacer element 58 is connected to the pivot arms 34 and 38, specifically at an attachment site 60, and, at the end of the connection element 58 remote from the attachment site 60, the bar 56 is connected to it in an articulated manner, via an eyelet 62.

According to FIGS. 5*a*) and *b*), the bar 56 is partially received in a cylinder 64, specifically with a portion 56*a* of the bar 56, and the bar 56 is able to move axially relative to the cylinder 64 in the longitudinal direction of the bar 56.

At least one spring 66 is also arranged in the cylinder 64. The pretensioning of the spring 66 can be adjusted and set by means of an abutment 67 which is connected to one end 69 of the bar 56, preferably via a thread arrangement.

During a pivoting of the pivot arms 34 to 40 about the pivot axes 42 and 44, the bar 56 executes (in addition to a tilting movement) an axial movement, oriented in its longitudinal direction, relative to the cylinder 64. This longitudinal movement is depicted in FIGS. 5*a*) and *b*) by a double arrow 68. In the case of an upwardly directed pivoting movement of the pivot arms 34 to 40, the bar 56 is moved toward the right in FIGS. 5*a*) and *b*), whereas, in the case of a downwardly directed pivoting movement of the pivot arms 34 to 40, the bar 56 is moved toward the left in FIGS. 5*a*) and b). FIG. 5*a*) shows the bar 56 in its position of maximum insertion in the cylinder 64. This corresponds to the pivot position of the pivot arms 34 to 40 in FIGS. 1 and 2, in which the arm support 12 is lowered to the maximum extent. The spring 66 is relaxed in this position, and, in the event of an upwardly directed pivoting movement of the pivot arms 34 to 40 in which the bar 56 is moved in the direction out of the cylinder, the spring 66 is tensioned, as is depicted in FIG. 5*b*). FIG. 5*b*) shows the bar 56 in its position of maximum extraction.

The cylinder 64 is connected to the carrying arms 36 and 40, specifically via a bow-shaped element 70 (see FIG. 1) which is connected to the pivot arms 36 and 40 at attachment sites 72 and to the cylinder 64 via a hinge 74. A relative tilting movement between the cylinder 64 and the bow-shaped element 70 is permitted via the hinge 74, but the cylinder 64 is held on the bow-shaped element so as to be immovable in its longitudinal direction.

According to FIG. 1, a passage 78, through which the cylinder 64 protrudes, is provided in the strut 32 of the base 16, the size of said passage 78 being sufficient to ensure that the cylinder 64 can execute the tilting movements necessary during the pivoting of the pivot arms 34 to 40.

The control mechanism 54 also comprises a freewheel coupling 80 with which the bar 56 interacts in order to effect a different running characteristics of the pivoting movements of the pivot arms 34 to 40 in the upward and downward directions and, consequently, of the height adjustment of the arm support 12.

The freewheel coupling 80 is shown on its own in FIGS. 4*a*) and *b*).

The freewheel coupling 80 comprises a first coupling element 82 and a second coupling element 84, which are shown on their own in FIGS. 3*a*) and *b*).

The coupling elements 82 and 84 are designed in the form of wheels which are rotatable about a common rotation axis 86 and are arranged concentrically with respect to this rotation axis 86 and one behind the other.

Figure 3:
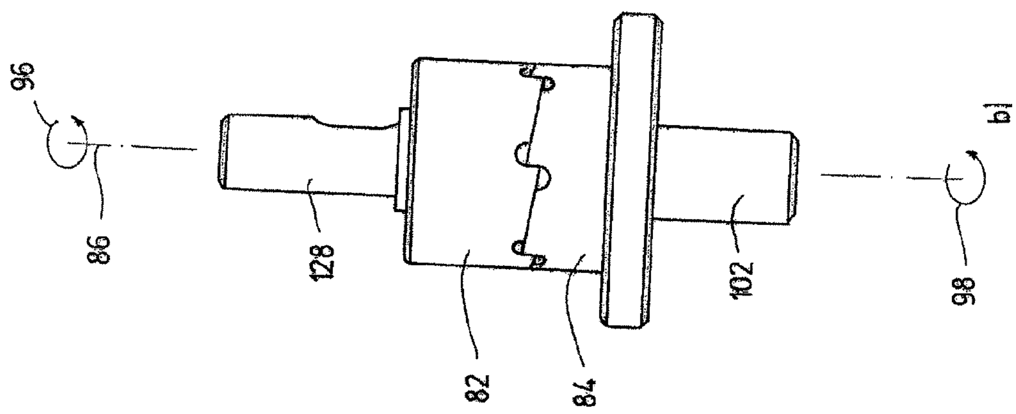
FIGS. 3*a*) and *b*) each show two coupling elements of a freewheel coupling of the armrest in FIGS. 1 and 2, FIG. 3*a*) showing the two coupling elements in a first operating position, and FIG. 3*b*) showing them in a second operating position.
Figure 3:
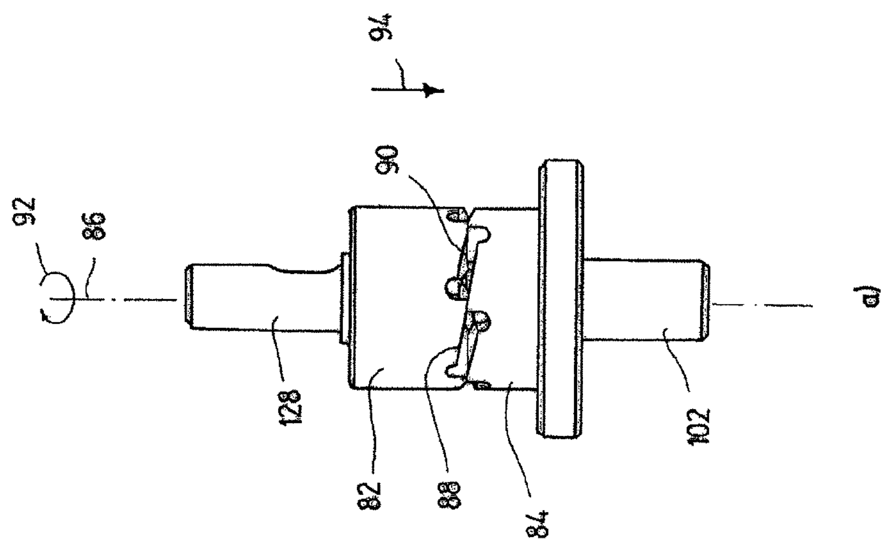

The first coupling element 82 and the second coupling element 84 have, on their end faces, and with respect to the rotation axis 86, a complementary oblique toothing 88 (coupling element 82) and 90 (coupling element 84). The shape of the oblique toothings 88 and 90 is shown in FIG. 3.

Upon a rotation of the first coupling element 82 about the rotation axis 86 in the direction of an arrow 92, the oblique toothing has the effect that the end face of the coupling element 82 slides on the coupling element 84, such that the second coupling element 84 is not moved in rotation during such a rotation of the first coupling element 82. The shape of the oblique toothing 88 and 90 means that, during a rotation of the coupling element 82 in the direction of the arrow 92, the second coupling element 84 is also pushed away in the direction of an arrow 94 in FIG. 3*a*), such that the second coupling element 84 is moved away from the first coupling element 82 by means of the rotational movement of the first coupling element 82 in the direction of the arrow 92, and specifically to the extent as shown in FIG. 3*a*). The second coupling element 84 is for this purpose axially movable in the direction of the rotation axis 86.

Figure 4:
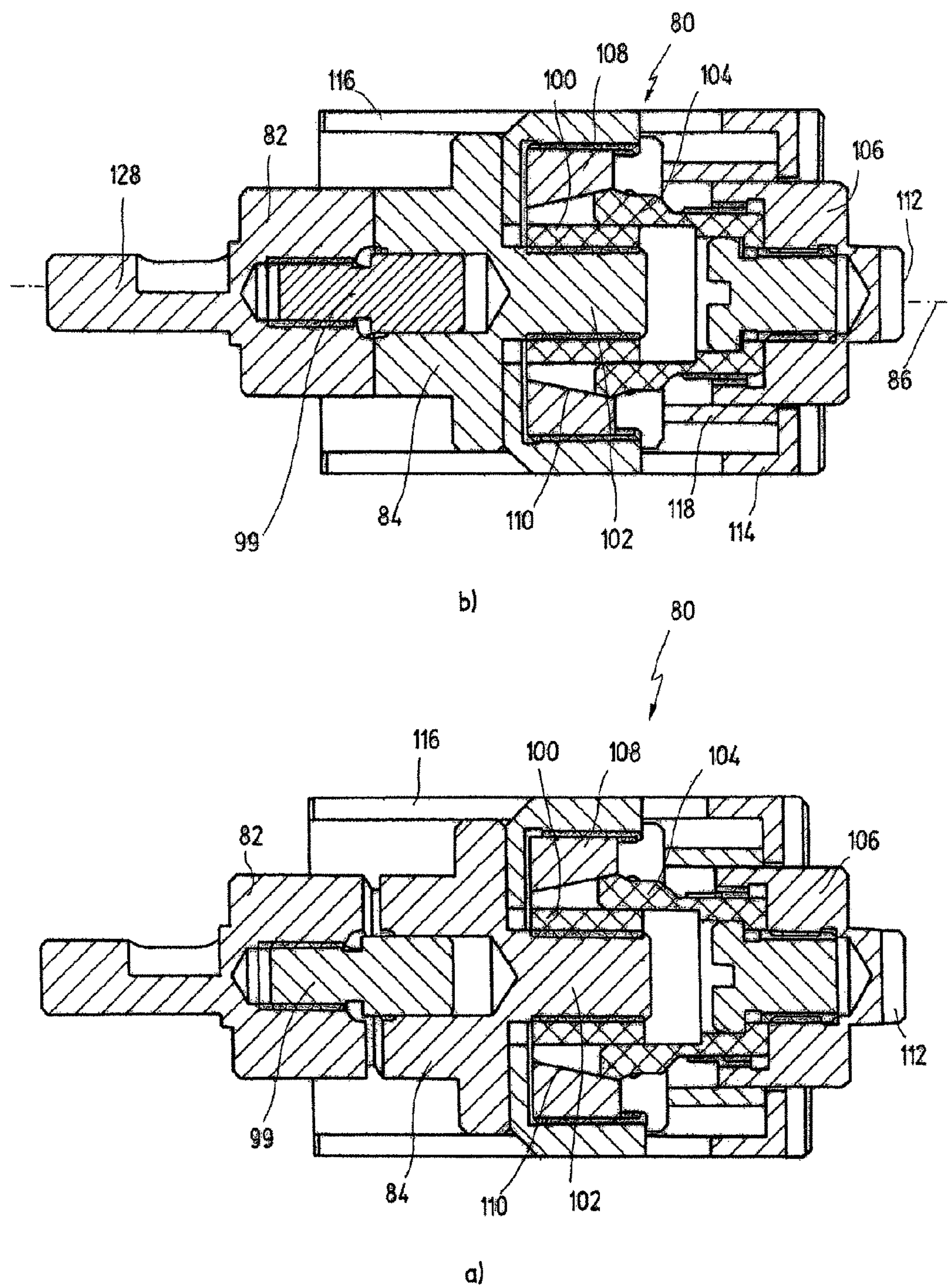
FIGS. 4*a*) and *b*) show longitudinal sections of the freewheel coupling of the armrest in FIGS. 1 and 2, with FIG. 4*a*) showing the freewheel coupling in an operating state corresponding to FIG. 3*a*), and FIG. 4*b*) showing it in an operating state corresponding to FIG. 3*b*)

According to FIG. 4, the first coupling element 82 and the second coupling element 84 are centered relative to one another via a pin 99, the pin 99 being fixedly connected to the first coupling element 82, whereas the second coupling element 84 is rotatable relative to the pin 99 about the rotation axis 86 and is additionally axially displaceable in the direction of the rotation axis 86.

During a rotation of the first coupling element 82 about the rotation axis 86 in the direction of an arrow 96, that is to say in the opposite direction of rotation from the one in FIG. 3*a*), the oblique toothing 88 of the first coupling element 82 comes into a form-fit engagement with the oblique toothing 90 of the second coupling element 84, as a result of which the second coupling element 84 is moved in rotation by the first coupling element 82, as is depicted by an arrow 98 in FIG. 3*b*).

FIG. 3*a*) accordingly represents the freewheel state of the freewheel coupling 80, whereas FIG. 3*b*) shows the operating state of the coupling 80 in which the second coupling element 84 also turns.

The operating state in FIG. 4*a*) corresponds to the operating state in FIG. 3*a*), and the operating state in FIG. 4*b*) corresponds to the operating state in FIG. 3*b*).

Referring again to FIG. 4, the second coupling element 84 cooperates with a brake element 100 which brakes a rotation of the second coupling element 84 about the rotation axis 86 by frictional engagement between the brake element 100 and the second coupling element 84. The brake element 100, which is shown in perspective in the enlarged detail in FIG. 2, is made of an elastic material, for example silicone.

The brake element 100 is arranged on a shaft extension 102 of the second coupling element 84, which shaft extension 102 is rotatable relative to the nonrotatable brake element 100.

The braking action of the brake element 100 can be adjusted by adjusting the contact pressure of the brake element 100 on the shaft extension 102 of the second coupling element 84. For this purpose, a clamping device is provided which comprises a clamping jaw 104 and an axial adjustment mechanism in the form of an adjustment sleeve 106, the clamping jaw cooperating with a counter-holder 108 which has a narrowing ramp 110, such that, when the clamping jaw 104 is pushed forward via the adjustment sleeve 106, the clamping jaw 104 presses the brake element 100 with increasing pressure onto the shaft extension 102. According to the enlarged detail in FIG. 2, the adjustment sleeve 106 is provided with a slotted head 112 so as to be able to actuate the adjustment sleeve 106 with a screwdriver in order to adjust the braking action of the brake element 100.

The freewheel coupling 80 also comprises a housing part 114 which, via a guide slit or a guide groove 116, additionally permits the axial guiding of the second coupling element 84 together with the brake element 100 and the above-described clamping device. As has already been described, the axial mobility of the aforementioned parts is needed to ensure that the first coupling element 82 in the rotation direction according to arrow 92 in FIG. 3*a*) can push away the second coupling element 84 and the parts connected thereto, as is shown in FIG. 4*a*).

To ensure that the oblique toothing 90 of the second coupling element 84 can again automatically come into a form-fit engagement with the oblique toothing 88 of the first coupling element 82 in the event of a downward movement of the pivot arms 34 to 40, the second coupling element 84 is pretensioned in the direction of the first coupling element 82 by means of a spring 118. As has already been mentioned, the brake element 100 and the clamping device for the brake element 100 also move axially with the second coupling element 84.

The operative connection between the bar 56 and the freewheel coupling 80 will now be described.

In its longitudinal movement in the directions according to the double arrow 68 in FIGS. 5*a*) and *b*), the bar 56 drives the freewheel coupling 80, or to be more exact the bar 56 always drives the first coupling element 82. In order to drive the first coupling element 82, the bar 56 is connected to the first coupling element 82 via a gear arrangement 120, as is shown in FIGS. 5*a*) and *b*).

The gear arrangement 120 comprises a first toothed wheel 122 which meshes with a toothing 124 on a partial section of the bar 56. The toothed wheel 122 in turn meshes with a second toothed wheel 126 which is arranged on a shaft extension 128 of the first coupling element 82 and is connected in a rotationally fixed manner to the first coupling element 82. The first toothed wheel 122 has a greater diameter than the second toothed wheel 126, with the result that there is a speed of rotation transmission ratio of greater than 1.

As will be seen from FIGS. 5*a*) and *b*), the freewheel coupling 80 is oriented with respect to the bar 56 in such a way that the rotation axis 86 of the coupling elements 82 and 84 is oriented perpendicular to the axial direction of movement of the bar 56 according to the double arrow 68.

The gear arrangement 120 together with the freewheel coupling 80 is accommodated in a main housing 130, which is shown in isolation in the enlarged detail in FIG. 2, and which is secured on the cylinder 64 of the bar 56. The main housing 130 also comprises the housing part 114, which is shown in a detached state in the enlarged detail in FIG. 2.

The drive of the freewheel coupling 80 by the bar 56 is described with reference to FIGS. 5*b*). When the bar 56 is moved in the direction out of the cylinder 64, as is the case in the event of an upward pivoting of the pivot arms 34 to 40, the first toothed wheel 122 is set in rotation in the counterclockwise direction in the drawing, as a result of which the second toothed wheel 126 is in turn set in rotation in the clockwise direction. In this way, the first coupling element 82 turns in the direction of the arrow 92 in FIG. 3*a*), such that the first coupling element 82 runs free, that is to say the second coupling element 84 is not driven along with it.

In the event of an opposite movement of the bar 56 for downward pivoting of the pivot arms 34 to 40, the direction of rotation of the toothed wheels 122 to 126 is exactly the reverse, such that the first coupling element 82 turns in the direction of the arrow 96 according to FIG. 3*b*). In this direction of rotation, a form fit is established between the oblique toothing 88 and the oblique toothing 90, as a result of which the second coupling element 84 is likewise set in rotation. However, since the rotation of the second coupling element 84 is frictionally braked by the brake element 100, this movement of the bar 56 and, consequently, the downwardly directed pivoting movement of the pivot arms 34 to 40 is braked or attenuated.

In this way, the arm support 12 of the armrest 10 can be moved up and down between two end positions, the upward movement of the arm support 12 running smoothly, while the downward movement of the arm support 12 runs more slowly, and therefore in a controlled way, because of the braking action and depending on how the braking action is set. The upward movement of the arm support 12 is counteracted only by the force of the spring 66, which tensions more and more during the upward movement of the arm support 12 (see FIGS. 5*b*).

The spring 66 is preferably designed in such a way that it permits a controlled lowering of the arm support 12 counter to the braking force of the brake element, without additional force being applied by the user.

FIG. 6*a*) shows an operating state of the armrest 10 which represents the lowermost position of the arm support 12, in which position the pivot arms 34 to 40 are pivoted downward and the bar 56 is driven into the cylinder 64.

FIG. 6*b*) shows, by contrast, an operating state of the armrest 10 in which the arm support 12 is raised relative to the position in FIG. 6*a*). The bar 56 is accordingly drawn a distance out of the cylinder 64.

To ensure that the arm support 12, in the position shown in FIG. 6*b*), is locked securely against undesired lowering, a catch 132 is provided, which is described in more detail below with reference to FIGS. 7 and 8.

The catch 132 is designed in such a way that it blocks the longitudinally directed movement of the bar 56 when the catch is in its blocking position, whereas the catch can be released in order to enable the longitudinally directed movement of the bar 56. In the illustrative embodiment shown, the catch 132 is designed such that it can block the movement of the bar 56 relative to the cylinder 64.

The catch 132 comprises a bolt 134, one end of which is articulated on the main housing 130, fixed to the cylinder, so as to be pivotable about a tilt axis 136.

The bolt 134 comprises a passage 138 through which the bar 56 extends. Depending on the state of tilting of the bolt 134 about the tilt axis 136, the bar 56 extends either perpendicularly or obliquely through the passage 138.

FIG. 8*a*) shows the catch 132 and the bar 56 on their own, on an enlarged scale. The position of the bolt 134 of the catch 132 in FIG. 8*a*) corresponds to the operating state in FIG. 7*a*). It will be seen from FIG. 8*a*) that the bolt 134 is tilted about the tilt axis 136 in such a way that the bar 56 extends obliquely through the passage 138, as a result of which the bar 56 is clamped in the passage by being jammed on the edge of the passage 138.

By contrast, FIG. 8*b*) shows the arrangement of catch 132 and bar 56 in a state that corresponds to the operating state of the armrest in FIG. 7*b*), in which the bolt 134 of the catch 132 is tilted about the tilt axis 136 in such a way that the bar 56 now extends perpendicularly through the passage 138. In this position of the catch 132, the bar 56 is movable in its longitudinal direction.

Referring to FIGS. 7*a* and *b*), it is now described how the catch 132 is activated for blocking the mobility of the bar 56 and how it is released for enabling the latter.

An end 140 of the bolt 134 remote from the tilt axis 136 is connected to a lever part 144 via a pull/push element 142, for example a bar or strut, the connection of the pull/push element 142 to the end 140 of the bolt 134 and to the lever part 144 being an articulated one.

As has already been described above, the arm support 12 is connected via the bearing element 46 to the strut 48, which is connected to the pivot arms 34 to 40. However, the connection of the bearing element 46 to the strut 48 is not rigid, and instead is effected via two further struts 146 and 148 which are connected in an articulated manner to the strut 48, such that the bearing element 46, and consequently the arm support 12, can move slightly relative to the pivot arms 34 to 40. This mobility is directed substantially vertically corresponding to an articulation of the struts 146 and 148 via substantially horizontal pivot axes 150, 152.

The above-described lever part 144 forms an L-shaped lever, such that a pivoting of the strut 148 about the pivot axis 152 at the same time effects a pivoting of the lever part 144, as a result of which the pull/push element 142 is in turn moved in its longitudinal direction.

FIG. 7*a*) shows a state in which the arm support 12, and consequently the bearing element 46, is located, relative to the pivot arms 34 to 40, in the maximally downwardly pivoted position about the pivot axes 150 and 152. The arm support 12 automatically adopts this position because of its force of gravity, and also when an operator rests his arm on the arm support 12. In this state, the lever part 144 presses the push/pull element 142 in the direction of an arrow 154, as a result of which the bolt 134 of the catch 132, as shown in FIG. 8*a*), is tilted about the tilt axis 136 in such a way that the bar 56 extends obliquely through the passage 138 and is thus clamped. The clamping effect is higher, the greater the bearing force applied to the arm support 12.

In order to free the catch 132 now, so that the bar 56 can move relative to the cylinder 64, for example in order to lower the arm support 12 starting from FIG. 7*a*), the arm support is lifted slightly according to an arrow 156 in FIG. 7*b*). This slight lifting does not cause any upwardly directed pivoting movement of the pivot arms 34 to 40, but only a relative movement of the arm support 12 with respect to the pivot arms 34 to 40. In this relative movement, the lever part 144 draws the pull/push element 142 in the direction of an arrow 158, as a result of which the bolt 134 of the catch 132 is tilted about the tilt axis 136 in such a way that the bar 56 now extends perpendicularly through the passage 138 and can now move relative to the passage 138. Since the mobility of the bar 56 is now enabled, the arm support 12 can be lowered. The lowering is obtained by the action of the spring 66, the arm support 12 being maintained in the slightly raised position relative to the pivot arms 38 to 40 (FIG. 7*b*)) in order to keep the catch 132 unlocked. The brake element 100 ensures a controlled lowering at a speed corresponding to the selected braking action.

Releasing the catch 132 requires only a slight lifting of the arm support 12, and this can be done with the same arm that is resting in the arm support. To ensure that the arm support 12 can be lifted with this arm, the arm support 12 is designed in the form of a shell 160 having substantially the shape of a C, such that a section 162 reaches at least as far as the top face of the arm received in the shell 160.

Figure 6:
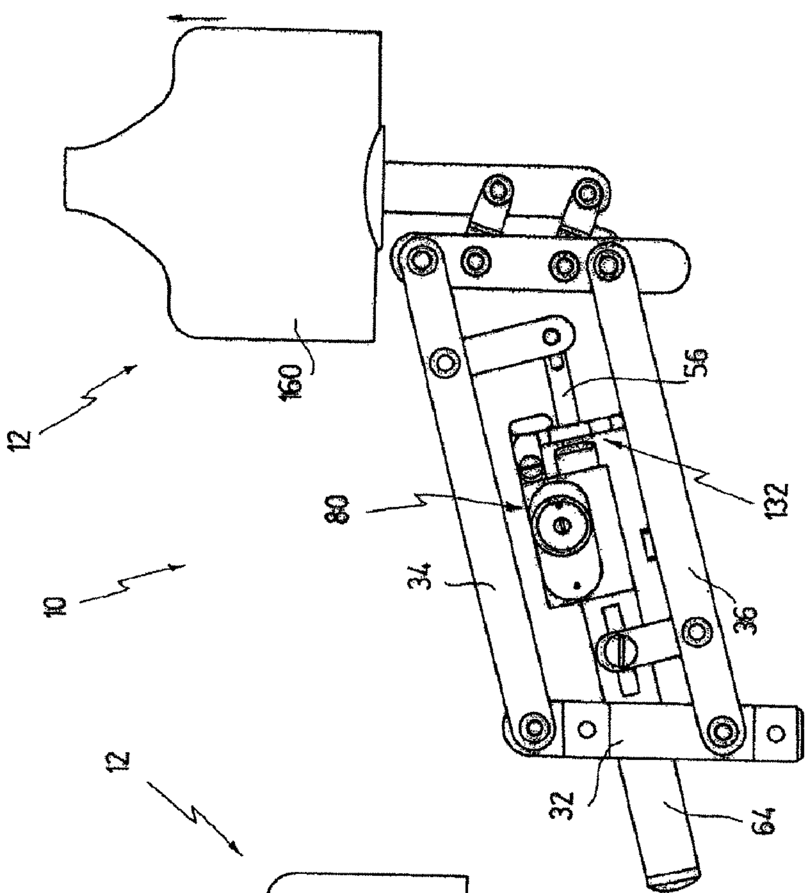
FIGS. 6*a*) and *b*) show the surgical armrest in FIGS. 1 and 2, but with some parts being omitted compared to FIGS. 1 and 2, with FIG. 6*a*) showing the armrest in a first operating state, and FIG. 6*b*) showing it in a second operating state.
Figure 6:
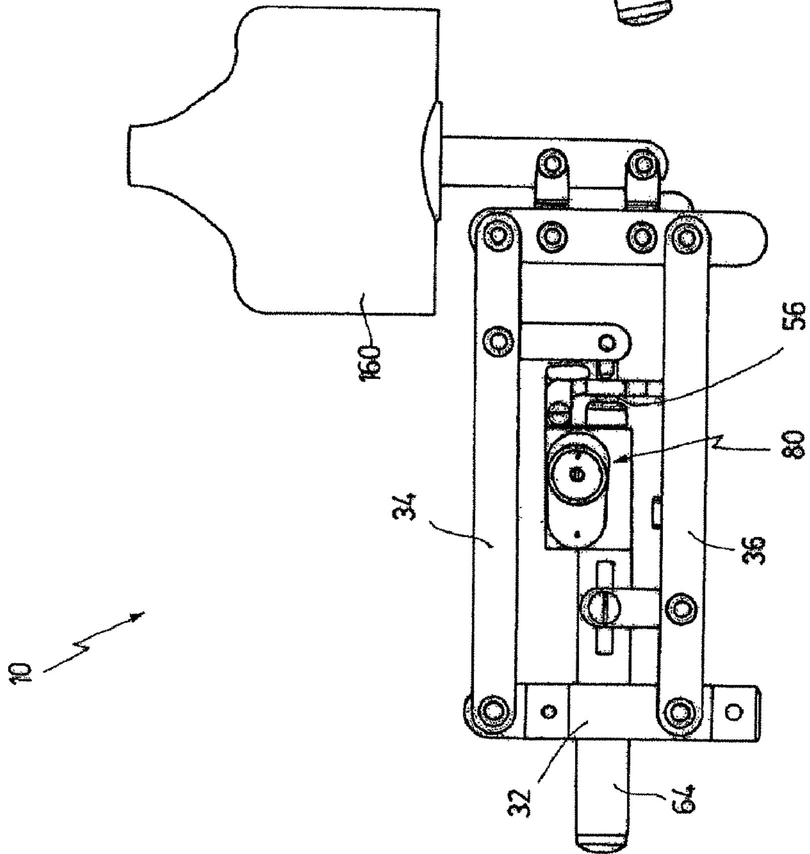
Figure 7:
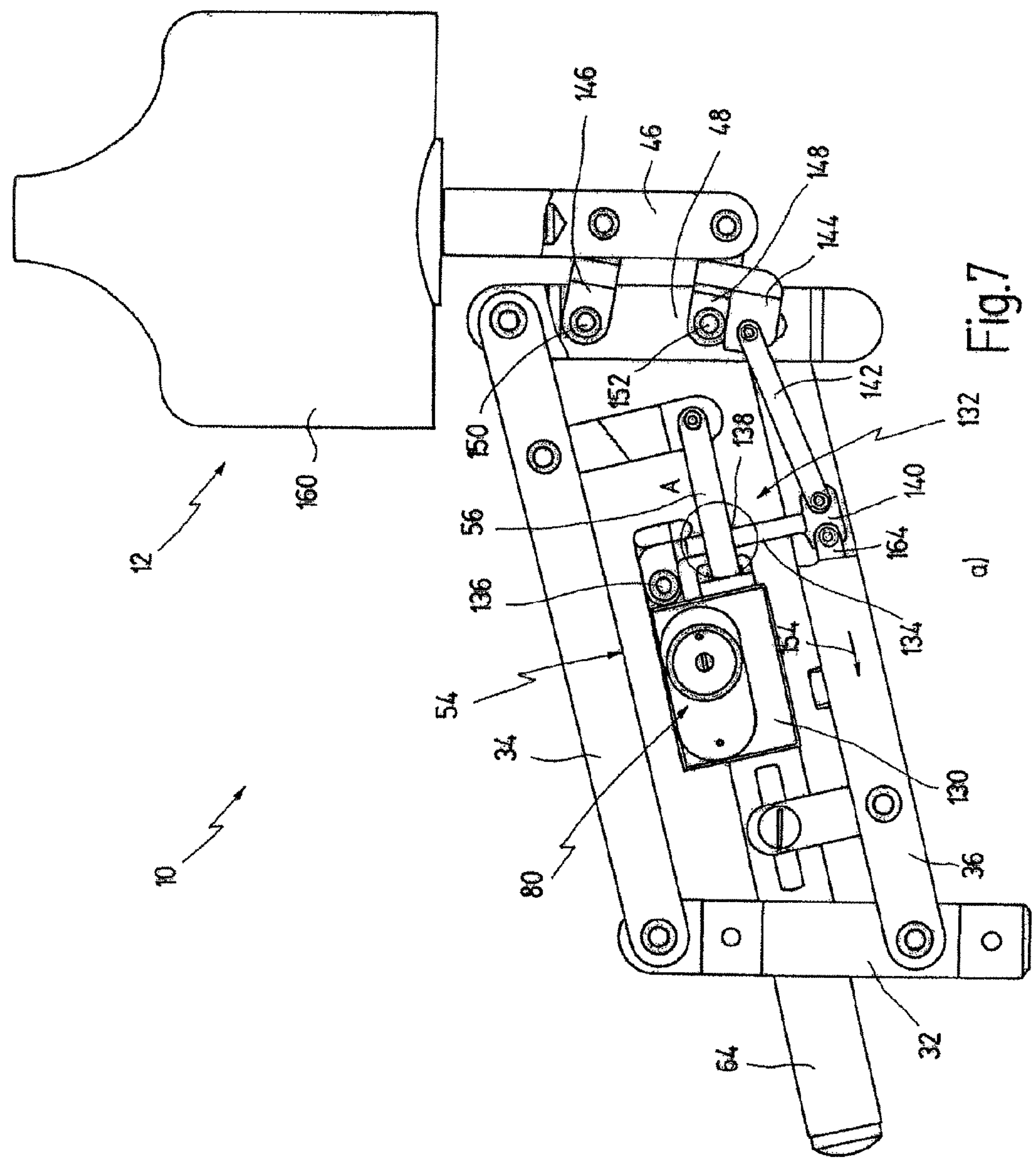
FIGS. 7*a*) and *b*) show the surgical armrest, with some parts being omitted compared to FIGS. 1 and 2, in each case In a side view in different operating states of the armrest.
Figure 8:
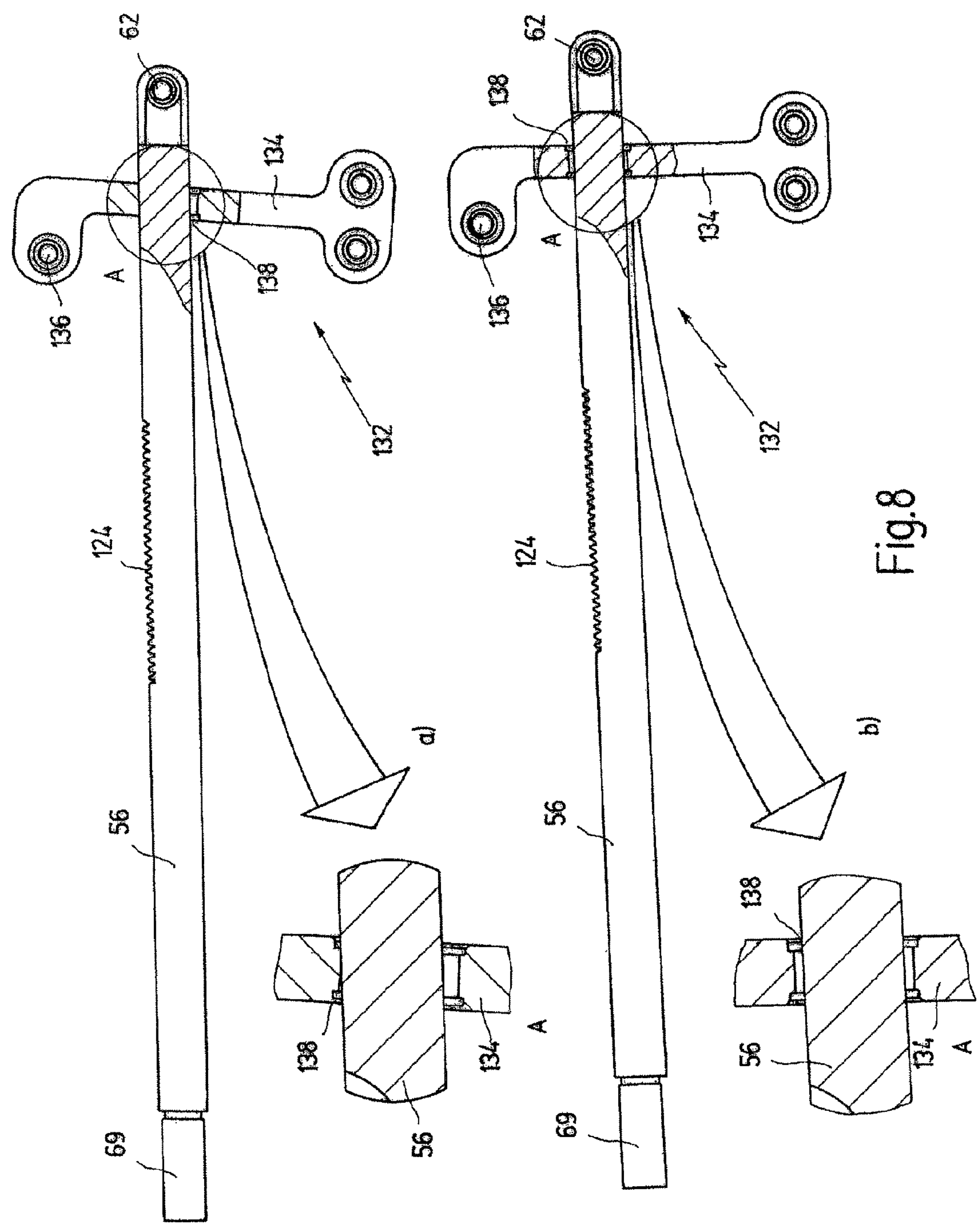
FIGS. 8*a*) and *b*) show further details of the surgical armrest in FIGS. 1 and 2, in two different operating states.

As will be seen from FIGS. 1, 6 and 7, the lower end 140 of the bolt 134, the pull/push element 142, the lever part 144 and the struts 146, 148 are partially recessed within the pivot arm 40 and strut 48.

Moreover, the lower end 140 of the bolt 134 is connected via a further pull element 164 to a tensioning spring (not shown) in the pivot arm 40, in order to ensure that the bolt 134 is pretensioned into the locking position according to FIG. 8*a*).

What is claimed is:

1. A surgical armrest, comprising an arm support, a carrying structure for carrying said arm support, said carrying structure having a base and at least one pivot arm having a first end articulated on said base so as to pivot about an at least approximately horizontal pivot axis, and a second end connected to said arm support, such that a pivoting of said at least one pivot arm about said pivot axis causes a height adjustment of said arm support, and a control mechanism for controlling said at least one pivot arm for alternately permitting a fixing and a pivoting of said at least one pivot arm in downward direction and in upward direction, said control mechanism having at least one bar which is movable, at least in a longitudinal direction of said bar, upon pivoting of said at least one pivot arm, said control mechanism further having a freewheel coupling having a first coupling element and a second coupling element, said first coupling element being driven by said bar and being freely movable relative to said second coupling element upon an upward movement of said at least one pivot arm, and, upon a downward movement of said at least one pivot arm, driving said second coupling element, and said second coupling element being braked by means of at least one brake element.

2. The armrest of claim 1, wherein said first coupling element and said second coupling element are in connection with one another via a form-fit engagement during said downward movement of said at least one pivot arm, whereas, during said upward movement of said at least one pivot arm, said form-fit engagement is cancelled by said second coupling element being spaced away from said first coupling element.

3. The armrest of claim 1, wherein said first coupling element and said second coupling element are rotatable about a common rotation axis and, on end faces of said first coupling element and said second coupling element directed toward one another, have a complementary oblique toothing which, in one direction of rotation of said first coupling element, causes a pushing-away of said second coupling element and, in an opposite direction of rotation of said first coupling element, causes a rotational movement of said second coupling element.

4. The armrest of claim 3, wherein said second coupling element is axially movable in direction of said rotation axis and is pretensioned in direction toward said first coupling element.

5. The armrest of claim 3, wherein said common rotation axis extends at least approximately perpendicular to said longitudinal direction of movement of said bar.

6. The armrest of claim 1, wherein said bar drives said first coupling element via a gear arrangement.

7. The armrest of claim 6, wherein said gear arrangement has at least one toothed wheel that meshes with a toothing of said bar.

8. The armrest of claim 7, wherein said gear arrangement comprises at least two toothed wheels that mesh with one another.

9. The armrest of claim 8, wherein said at least two toothed wheels have a different diameter with respect to one another.

10. The armrest of claim 1, wherein a braking action brought about by said brake element is adjustable.

11. The armrest of claim 10, wherein said brake element is made from an elastic material, and wherein a clamping device is operatively connected to said brake element in order to vary a contact pressure of said brake element on said second coupling element.

12. The armrest of claim 1, wherein said bar is assigned at least one spring which is tensioned during said upward movement of said at least one pivot arm and is relaxed during said downward movement of said at least one pivot arm.

13. The armrest of claim 12, wherein said at least one spring is configured such that said at least one pivot arm is pivoted in downward direction by said spring while counteracted by said brake element.

14. The armrest of claim 1, wherein said at least one pivot arm is a first pivot arm, wherein said carrying structure comprises at least one second pivot arm which extends at least approximately parallel to said first pivot arm, and having a first end articulated on said base about a second pivot axis spaced vertically apart from said pivot axis of said first pivot arm, and a second end connected to said arm support, wherein said bar is partially received in a cylinder so as to be movable relative to said cylinder, said cylinder being secured on said second pivot arm.

15. The armrest of claim 14, wherein said freewheel coupling comprises a housing which is secured on said cylinder.

16. The armrest of claim 1, wherein said bar is provided with a releasable catch which blocks said bar so that said bar is axially immovable, while said bar is free after release of said catch.

17. The armrest of claim 16, wherein said catch is formed by a bolt which has a passage for said bar, said bolt being able to be moved about a tilt axis into a first tilt position, in which said bar extends obliquely through said passage and is thus clamped on said passage, and into a second tilt position in which said bar extends substantially perpendicularly through said passage and is thus axially movable.

18. The armrest of claim 16, wherein said arm support is movable relative to said at least one pivot arm, and said catch is connected to said arm support in such a way that, by slight lifting of said arm support relative to said at least one pivot arm, said catch is transferred from a blocked position into a release position, and, by slight lowering of said arm support relative to said at least one pivot arm, is transferred into said blocked position again.

19. The armrest of claim 1, wherein said arm support is designed in such a way that it allows said arm support to be lifted by an arm of a user, which arm is resting on said arm support.

20. The armrest of claim 19, wherein said arm support is designed as a substantially C-shaped shell.

* * * * *